(12) United States Patent
Seegers et al.

(10) Patent No.: US 6,439,722 B1
(45) Date of Patent: *Aug. 27, 2002

(54) SYSTEM AND METHOD FOR SYNCHRONIZING THE APPEARANCE OF COLOR IMAGES

(75) Inventors: Björn Seegers, Munster; Thorsten Braun, Rheine-Mesum, both of (DE); Francis A. Lamy, Mamaroneck, NY (US)

(73) Assignee: GretagMacbeth, New Windsor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/520,453

(22) Filed: Mar. 8, 2000

Related U.S. Application Data

(63) Continuation-in-part of application No. 09/201,964, filed on Dec. 1, 1998, now Pat. No. 6,036,317.

(51) Int. Cl.[7] .................................................. A61B 3/02
(52) U.S. Cl. ....................................................... 351/243
(58) Field of Search .................................. 351/239, 242, 351/243, 224, 246; 600/558; 345/601, 600, 602, 603, 604, 605; 382/162, 164, 167

(56) References Cited

U.S. PATENT DOCUMENTS

| | | |
|---|---|---|
| 4,765,731 A | 8/1988 | Williams |
| 5,297,559 A | 3/1994 | Severns |
| 5,883,692 A | 3/1999 | Agonis et al. |
| 6,011,540 A * | 1/2000 | Berlin et al. ................. 345/601 |
| 6,036,317 A | 3/2000 | Seegers et al. |

OTHER PUBLICATIONS

Print–out of Web Site www.e–color.com/products/trueinternetcolor/welcome.html, pp. 1 and 2 of 2, print–out dated Jan. 28, 2000.
Print out of Web Site www.e–color.com/products/trueinternetcolor/solutions.html, pp. 1 and 2 of 2, print out dated Jan. 28, 2000.
Print out of Web Site www.e–color/corporate_babble/pr28.html.pp. 1 and 2 of 2, print out dated Jan. 28, 2000.
Print out of Web Site www.e–color.com/corporate_babble/pr40.htm.pp. 1 and 2 of 2, print out dated Jan. 28, 2000.
Print out of Web Site www.e–color.com/products/trueinternetcolor/tic.html.pp. 1 and 2 of 2 , print out dated Jan. 28, 2000.
Print out of Web Site www.e–color.com/products/trueinternetcolor/problem.html,pp. 1 and 2 of 2, print out dated Jan. 28, 2000.
Print out of "webreview.com—Accuarate Color on the Web" at Web Site www.webreview.com/p . . . e/index.html?wwwrrr_19990806–wt.tx, pp. 1 thru 5 of 5, print out dated Jan. 28, 2000.
Print–out of "Introduction to Color Management in Windows" at Web Site www.microsoft.com/hwdev/devdes/icm-wp.htm, pp. 1 thru 8 of 8, print-out dated Jan. 28, 2000.

* cited by examiner

Primary Examiner—George Manuel
(74) Attorney, Agent, or Firm—Cummings & Lockwood

(57) ABSTRACT

A system for color characterization of an self-illuminating imaging display device and synchronization of the appearance of color images displayed on a self-illuminating imaging device is disclosed which is configured to embed a color characterization program in a response to an initial browser based request for a color image to facilitate the color characterization of a self-illuminating imaging device associated with the browser, forward the embedded response to a web browser, and generate a profile characterizing the self-illuminating imaging device using the color characterization program. The system is further configured to modify a response to a subsequent browser based request for a color image by replacing the image tags associated with the color image with substitute image tags configured to effect a color transformation based upon the profile characterizing the self-illuminating imaging device, forward the modified response to the web browser, and transform the color image based upon the substitute image tags for display on the self-illuminating imaging device.

49 Claims, 4 Drawing Sheets

SYSTEM AND METHOD FOR SYNCHRONIZING THE APPEARANCE OF COLOR IMAGES

CROSS-REFERENCE TO RELATED APPLICATIONS

The subject application is a continuation-in-part of U.S. application Ser. No. 09/201,964 filed Dec. 1, 1998 now U.S. Pat. No. 6,036,317, the disclosure of which is herein incorporated by reference in its entirety.

BACKGROUND OF THE INVENTION

1. Field of the Invention

The subject invention relates to a system and method of spectral or colorimetric characterization of an image display device, and more particularly, to a system and method for characterizing a self-illuminating imaging device and synchronizing the appearance of color images displayed on the self-illuminating imaging device with images produced by internet web sites.

2. Background of the Related Art

As used herein, imaging devices should be understood to include computer monitors, flat screen displays, televisions, large image projectors and the like. Spectral or colorimetric characterization denotes the spectral or colorimetric description of the current imaging properties of an imaging system which, for example, can also consist of a combination of the actual monitor in conjunction with driver software and/or a graphics card.

The characterization of color monitors has typically been achieved with colorimeters equipped with filters adapted to the sensitivity of the eye (frequently designated as three-area or tri-stimulus colorimeters) or spectral sensors associated with a spectral photometer. Color profiles of the monitors are then produced with the aid of the measured data from these devices. However, known calorimeters have the disadvantage that the illumination conditions of the monitor environment are not taken into account.

A method of characterization is known wherein a visual match is performed with color sample fields. During this method, color samples are held alongside the imaging system to be examined so that a color field produced on the imaging system can be appropriately matched. However, this known method only provides an approximate solution, since to achieve a proper match, a sufficient illumination of the color sample field and the least possible incidence of light onto the monitor is necessary. This cannot be achieved using such a method, because the color sample fields are kept adjacent to the monitor and or the color field produced thereby.

It is well know that color images sent to any web browser by a web server will always have the same numerical color values associated therewith. However, those images may not appear the same on every monitor on which they are displayed. This becomes most problematic for e-commerce online retailers, as goods that appear to be one shade on a computer screen are quite different in actuality. Indeed, of the millions of consumers shopping online, it has been estimated that nearly 60% of them do not trust the color of the images they see on their monitors.

Systems have been developed to calibrate the images seen by a viewer and the image created by a web designer. One such system, developed by E-Color, Inc., requires a web designer to supply information about how their system displays color by embedding a color profile with their images. On the consumer side, the E-Color system requires a customer to calibrate their monitor by completing a one-time set up procedure at a Website. The procedure requires the customer to view a series of color patches and click on matching colors. In use, when an image with an embedded profile is served to a customer's browser, the server-based E-Color system reads the color profile and adjusts the image for the difference between the authoring system and the customer's display.

There are certain disadvantages associated with a server-based color management system, in that real time color transformations are performed at the server, rather than at the browser. Consequently, there is a large computational burden placed on the server, which can degrade service. Clearly, there is a need in the art for a color management system that overcomes the deficiencies of prior art systems.

SUMMARY OF THE INVENTION

The subject invention provides a system and method for colorimetric characterization and synchronization of a self-illuminating imaging device which overcomes the problems and deficiencies of the prior art. More particularly, the system and method of the subject invention is an innovative and simple to use method of synchronizing the appearance of color images on a color monitor with images produced by Website across the Internet or World Wide Web.

The subject invention is particularly adapted and configured to enable companies engaging in e-commerce to achieve the high color accuracy required to effectively sell products and services to consumers over the Internet. In addition, the system is designed to enable individuals to access and accurately view images, such as online digital photos. In essence, the subject invention provides computer users with the ability to enable accurate color viewing over the Internet, and to support color decision making across the World Wide Web with consistent quality.

In accordance with a preferred embodiment of the subject invention, a user is provided with a set of four transparent color filter films or foils each having known spectral or colorimetric reference values (red, green, blue and neutral gray). Preferably, each film includes a low tack adhesive to facilitate temporary fixation on the monitor screen during the characterization or set-up procedure, which will not leave an undesirable residue on the monitor screen.

When the user goes on-line and initially contacts a system-enabled Website, the user is offered the option of starting a system application or program that is automatically embedded in the first web page received from the web server. After commencing a set-up procedure, the user is instructed to place a first color film onto the monitor screen, within a "window" of nominal white space surrounded by a solid color border. Color adjustments are made by the user with a slider or similar color adjustment mechanism associated with the monitor until a visual color match is achieved between the color film and the surrounding solid color border, i.e., when the color impression of the surrounding color border corresponds to the color impression of the color signal generated by the transparent color filter film.

This visual matching process is then repeated for the other two color films, and for the gray film. From the slider settings made by the user, an optimum color transformation for the monitor is then computed based upon the known colorimetric reference values for the films, and a monitor profile is generated by the system. The monitor profile is then stored as a "cookie" in the browser software. On all subsequent visits to the system-enabled Website, the color transformation will automatically be applied at the browser level to downloaded images and web pages to provide accurate color images on the user's monitor.

In sum, a system is disclosed to facilitate the color characterization of a computer monitor and synchronization of the appearance of color images displayed on the monitor with color images produced by web sites across the internet. The system is configured to embed a color characterization program in a response to an initial browser based request for a color image to facilitate the color characterization of the monitor associated with the browser. It then forwards the embedded response to the browser, and generates a profile characterizing the monitor using the color characterization program.

The system is further configured to modify a response to a subsequent browser based request for a color image by replacing the image tags associated with the color image with substitute image tags configured to effect a color transformation based upon the profile characterizing the monitor. It then forwards the modified response to the web browser, and transforms the color image based upon the substitute image tags for display on the monitor. Since the color transformations occur at the browser, there is no computational burden placed on the server.

The subject invention is also directed to a system for synchronizing the appearance of color images on a self-illuminating imaging device which includes a workstation including a self-illuminating imaging device, a web browser operatively associated with workstation, and a color management program operatively associated with the web browser for performing color transformations upon color images received by the web browser and displayed on the self-illuminating imaging device. Preferably, the color management program is downloaded to the web browser from a web server. Alternatively, the color management program and the web browser are encoded on a computer-readable storage medium which may be loaded into the memory of the workstation. It is also envisioned that the color management program could be integrated into the workstation and stored in memory.

The subject invention is further directed to a system and method for profiling the colorimetric characteristics of an image projection device associated with a computer workstation. The system employs a set of color reference plates each having a predetermined spectral reflectance value associated therewith. During a profiling procedure, the color reference plates are sequentially placed onto a projection screen and illuminated by a projection beam. A visual match is performed for each reference plate by selectively adjusting the color of the projection beam. A color profile is generated for the projector based upon the selected color settings. The color profile is used to transform projected images.

These and other features of the system and method of the subject invention will become more readily apparent to those having ordinary skill in the art from the following detailed description of the invention taken in conjunction with the drawings.

BRIEF DESCRIPTION OF THE DRAWINGS

So that those having ordinary skill in the art to which the disclosed system and method appertains will more readily understand how to use the same, reference may be had to the drawings wherein.

These and other features of the system and method of the subject invention will become more readily apparent to those having ordinary skill in the art from the following detailed description of the preferred embodiments taken in conjunction with the drawings.

DETAILED DESCRIPTION OF THE PREFERRED EMBODIMENTS

Figure 1:
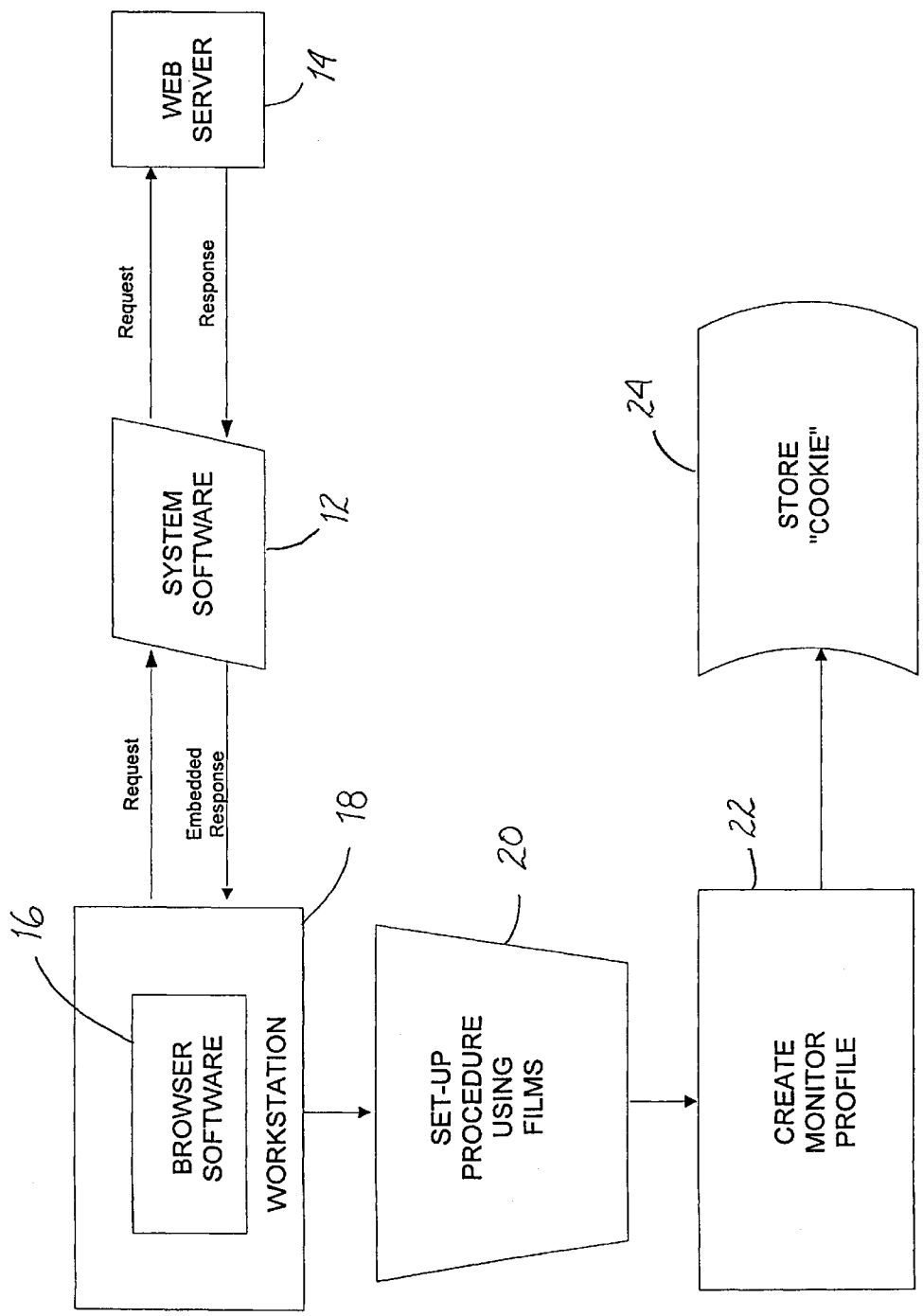
FIG. 1 is a schematic representation of the information flow between the Web server and the Website visitor during the initial visit to a Website enabled with the system of the subject invention.

Referring now to the drawings wherein like reference numerals identify similar elements of the subject invention, there is illustrated in FIG. 1 a schematic representation of the basic architecture and information flow pattern of the color characterization and synchronization system disclosed herein.

Referring to FIG. 1, the system basically comprises a system software application 12 which is operatively associated with and resides on a web server 14. The system software application 12 is preferably composed using Java and acts as an intermediary between the web server 14 and a visitor to a Website. More particularly, it transfers information between the web server 14 and the web browser software 16 resident on a workstation 18, while preventing direct access to the web server 14.

As illustrated in FIG. 1, when a visitor initially sends an HTML request for a color image to a system enabled Website associated with the web server 14, the web server responds by forwarding a response to the system software application 12. Thereupon, the system software application 12 embeds a color characterization application or program in the response. This would generally be located within the first page of the response. The color characterization application includes a set-up procedure adapted and configured to take a "snapshot" of the color characteristics of the monitor (the imaging device) associated with the workstation 18. The set-up procedure will be described in detail hereinbelow with respect to FIGS. 3 and 4.

It is envisioned that the color characterization application of the subject invention could be integrated into the system architecture of the workstation in the form of a Java application. Thus, it would be unnecessary for the set-up procedures to be embedded into the response, and downloaded to the browser from the server.

After the set-up procedure is conducted at process step 20, a profile is created at process step 22 which describes the color characteristics of the monitor. The profile, which will also be described in greater detail hereinbelow, is then stored in the memory of the workstation as a "cookie" at process step 24. The format of the cookie serves the purpose of recording as compactly as possible the numerical values required to fully describe the color characteristics of a color monitor. In an embodiment of the subject invention wherein the color characterization application resides at the workstation, the profile would be stored in memory as a conventional ICC (International Color Consortium) profile.

Figure 2:
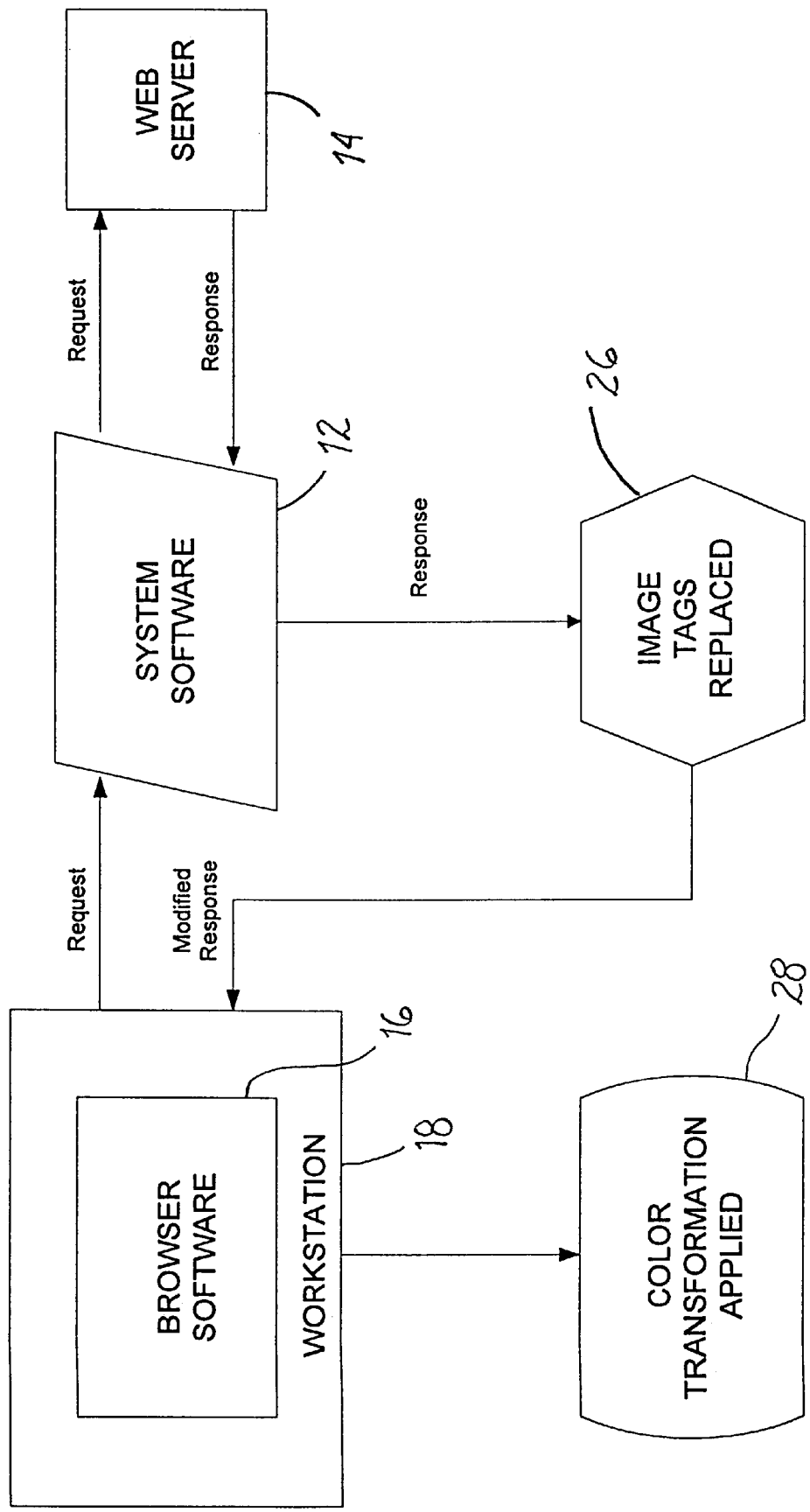
FIG. 2 is a schematic representation of the information flow between the Web server and the Website visitor during subsequent visits to the system enabled Website.

Referring to FIG. 2, on subsequent visits to a system enabled Website, the system software application 12 receives an HTML request for a color image from the browser software 16 associated with workstation 18 and forwards the request to the web server 14. The system software then receives the response, generally in the form of a web page, and modifies the HTML code of the response at process step 26 by replacing or substituting the "image tags" associated therewith with corresponding "applet tags" configured to facilitate color transformations based upon the profiled color characteristics of the monitor.

The modified response in then forwarded to workstation 18. Upon receipt by the browser software 16, the applet tags take control of the image display operations. At such a time, the color image associated with the response is transformed at process step 28 based upon the monitor profile stored at process step 24. Color transformation is performed by a Color Management Module (CMM) that is downloaded from the web server 14 to the browser software 16 together with the modified response. Once transformed, the color image is accurately displayed on the monitor. It is envisioned, and well within the scope of the subject invention, that the CMM could be part of the web browser architecture. For example, the web browser and the CMM could both be encoded on a computer-readable storage medium which would be loaded into the workstation. Alternatively, the CMM could be stored in the memory of the workstation as a resident application.

The CMM is an extremely compact application, preferably less than 30 kilobytes in size. Therefore, it will occupy an insubstantial amount of memory space at the browser on the workstation 18. During operation, all color conversion and color space transformations are performed locally at the workstation by the CMM, thus imposing no computational burden on the web server 12. Moreover, the web server does not have to recalculate image values every time a user connects with a system-enabled Website.

Figure 3:
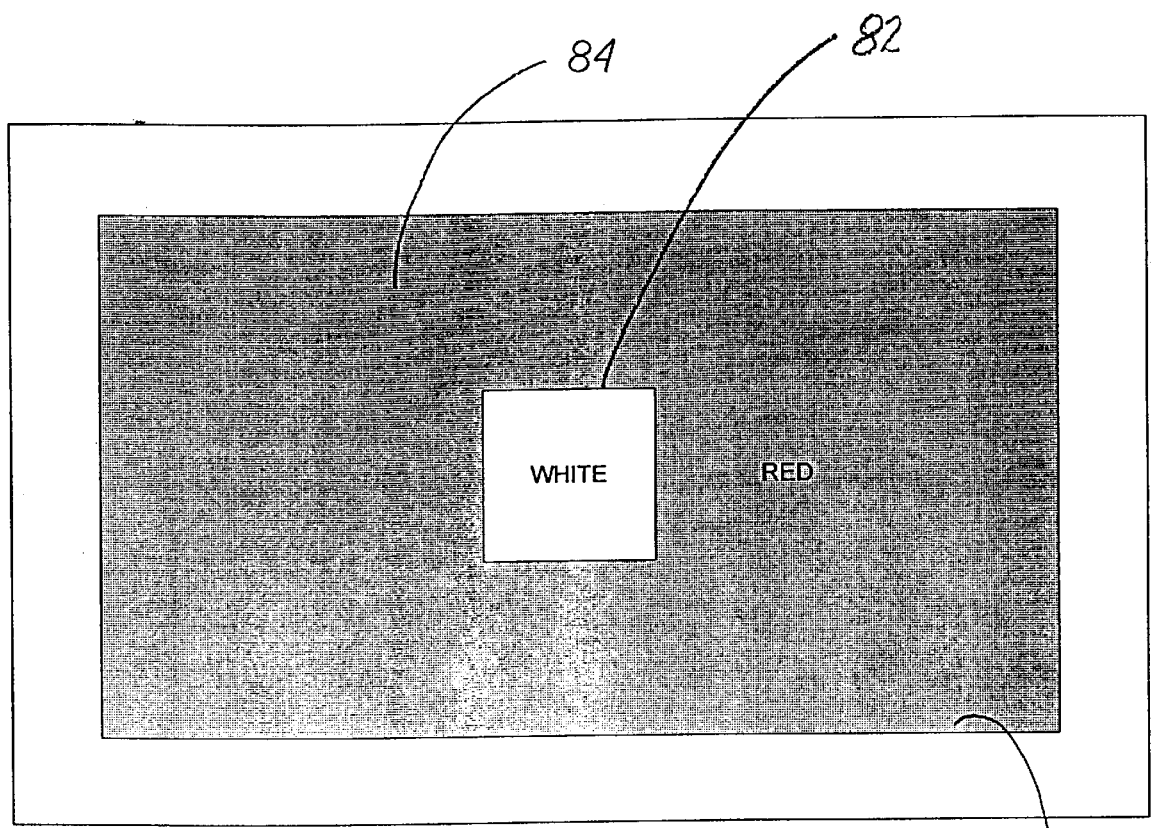
FIG. 3 illustrates a CRT monitor displaying a white region bounded by a red color region.
Figure 4:
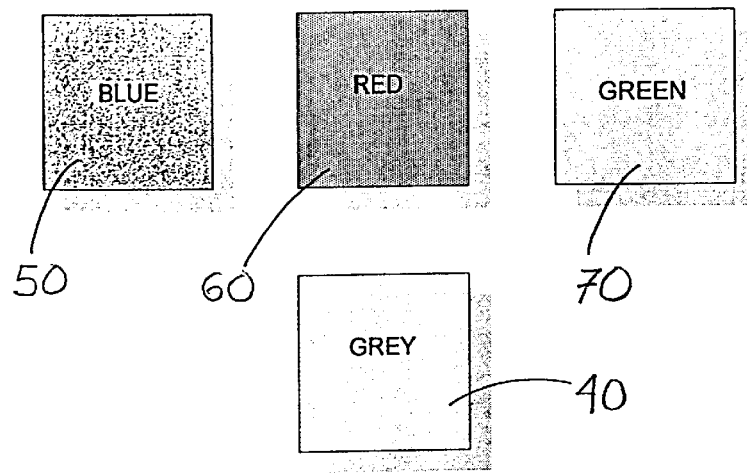
FIG. 4 is an illustration of red, green, blue and gray films dimensioned and configured to interact with the white region displayed in FIG. 3.

Referring now to FIGS. 3 and 4, the set-up procedure discussed briefly hereinabove is performed using a computer aided visual matching process. In the method of the subject invention, a series of four visual color matches are performed using a set of four transparent color films or foils. The set has a gray film 40 and three primary color films including a blue film 50, a red film 60 and a green film 70. Each film in the set has a known spectral or colorimetric reference value, and each of the four colors are represented by three numerical values. Thus, the set will yield twelve (12) profiling values.

After commencing a set-up procedure at the browser level in process step 20, the user is instructed to place a first color film onto the monitor screen 80, within a "window" or region of predefined color, such as, for example, a region of nominal white space 82 surrounded by a solid color border region 84. In the illustrated example of FIG. 3, the border region 84 is red, and the red filter film 60 would be employed to perform a visual color match therewith. During the set-up procedure, color adjustments are made by the user with a slider or similar color adjustment mechanism associated with the monitor 80 until a visual color match is achieved between the color film 60 and the surrounding solid color border 84, i.e., when the color impression of the surrounding color border region 84 corresponds to the color impression of the color signal generated by the transparent color filter film 60.

At step 20, this process is then repeated for the other two primary color films (i.e., the green film 50 and blue film 70), and for the gray film 40. From the slider settings made by the user, an optimum color transformation for the monitor is then computed by the color characterization program at process step 22 based upon the known colorimetric reference values for the films, and a monitor profile is generated by the system. In essence, the profile serves to describe the imperfections associated with the monitor. This profile is then stored as a cookie on the workstation associated with the monitor at process step 24, and is used to facilitate color transformations of images subsequently received by the web browser at process step 28. The browser-based color transformation essentially nullifies the imperfections of the monitor.

Those skilled in the art will readily appreciate that an additive color system, such as that which is described herein, is defined by its primary colors, in addition to the "gamma ramps" of the primaries. These ramps are often simplified as a single gamma value for each primary color. The gamma value serves to designate the slope of the actual gamma curve defined thereby. It is also well known that the primary colors are defined by three calorimetric coordinates in XYZ "device independent" space. Therefore, the model of a CRT monitor consists of twelve (12) numerical values: the three XYZ coordinates of each of the three primary colors (red, green and blue), as well as the three gamma values for each of the primaries. These twelve values correspond to the twelve numerical profiling values used to characterize the self-illuminating imaging device during the set-up procedure described hereinabove.

As described hereinabove, the set-up procedure at process step 20 involves sequential placement of the four color films on a region of nominal white space generated by the monitor (see FIG. 3). However, because the field upon which the color films are placed is not truly white, that color, in conjunction with the color of the films, will have the effect to maximize the distance (in colorimetric terms: in the XYZ space) between the three characterization points. This greatly enhances the precision and consistency of the subject system and method over simpler and less-effective calibration applications employed in the art.

It should be appreciated by those skilled in the art that color calibration of a device is distinct from color characterization of a device in that calibration does not enable accurate color reproduction. It only helps to better represent neutral tones, or setting-up brightness and contrast. Characterization, on the other hand, takes a "snapshot" of the color characteristics of the monitor and enables the transformation between LAB data and the specific monitor's RGB, and thus includes the actual gamma and the calorimetric coordinates of the primaries.

It is envisioned that the system and method of the subject invention can be used to achieve a higher degree of characterization, for a more color sensitive group of professional users, such as, photographers, advertising agencies and designers. In this instance a fifth color film or foil can be provided to enable a quality check so that the user can judge for themselves whether the monitor has been properly characterized during the set-up procedure.

It is also envisioned that the system and method of the subject invention can be modified to characterize Liquid Crystal Display (LCD) and flat screen imaging devices. In such an instance, the same four films or foils (red, green, blue and gray) would be utilized in conjunction with several different color backgrounds. This will provide the required control points to characterize these types of imaging devices. In addition, because the spatial model of a flat screen display has a more complex geometry than a conventional CRT display, a greater number of numerical values may be required to characterize the device. In such instances, the white point values could be used for characterization.

Figure 5:
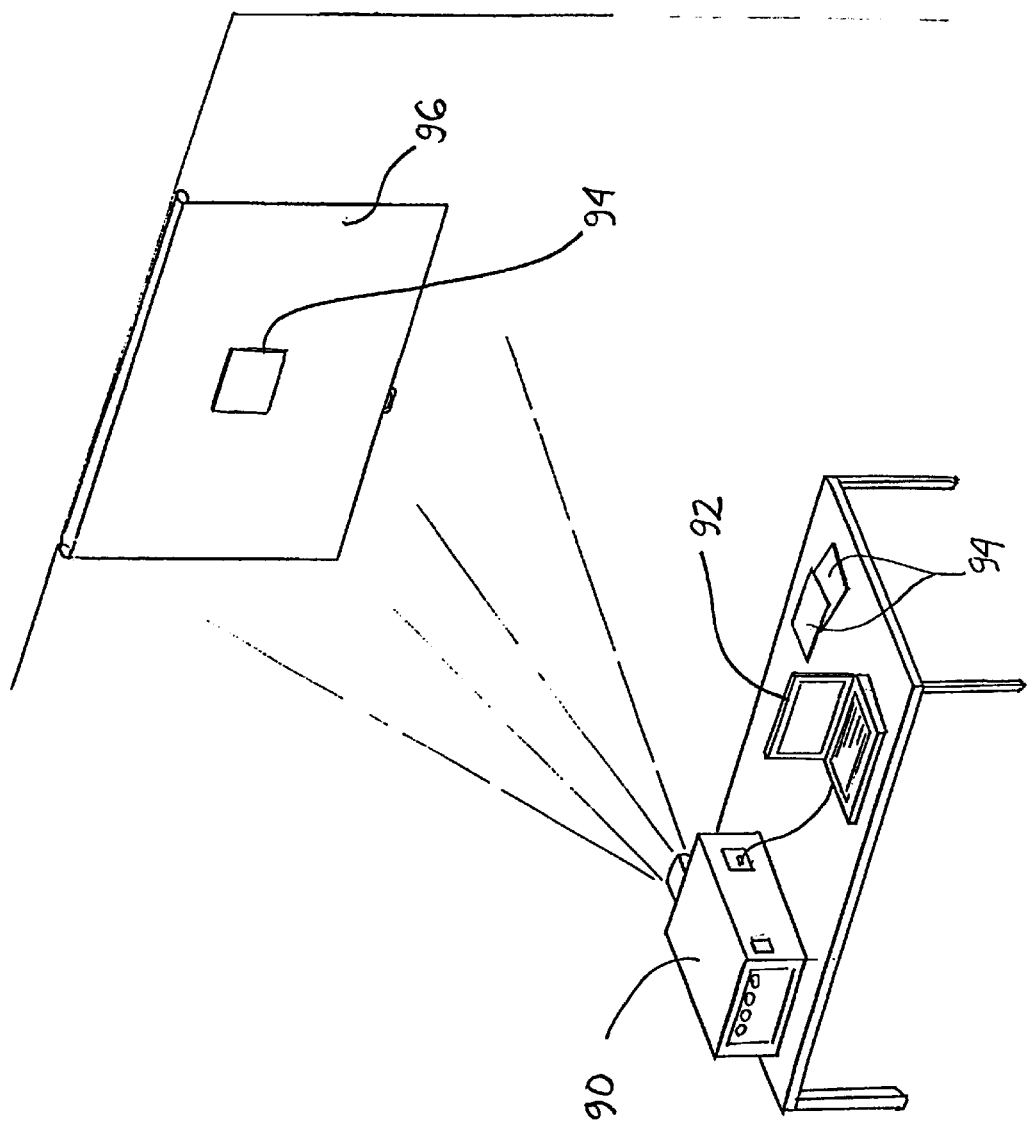
FIG. 5 illustrates an image projection device and associated computer workstation during a profiling procedure wherein the color characteristics of the projector are determined using a set of color reference plates each having a predetermined spectral reflectance value associated therewith.

Referring to FIG. 5, the subject invention is also directed to a system and method for characterizing the color characteristics of an image projection device 90 utilized in conjunction with a computer workstation 92. It has been found that colors displayed on a large image projection device can vary as a result of the graphics card installed in the workstation, the way in which the projector is setup, or the quality and characteristics of the canvas or screen upon which the projection is displayed. To overcome this problem, the calorimetric characteristics of the projection can be determined and used by the workstation. More particularly, a profile can be created to represent the color characteristics of the device. This profile can then be used to transform the display data produced by the workstation in such a manner so that the color images displayed by the projector will be as intended by the designer.

In accordance with an embodiment of the subject invention, the calorimetric characteristics of the image projection device 90 are determined using a set of color reference plates 94, each having a known spectral reflectance value associated therewith. During a profiling procedure, the color reference plates 94 are sequentially placed onto the projection screen 96 and illuminated by the projection beam. Preferably, the reference plates are illuminated with a nominal white beam. Thereafter, a visual matching process takes place by matching primary (RGB) color combinations of the projection beam with each color reference plate using a selection mechanism associated with the projection device 90. After finding a match for each color reference plate 94, a color profile is generated for the projection device 90. This is similar to the process described above, wherein a set of transparent color films or foils are used to characterize and profile a computer monitor.

Although the systems and methods disclosed herein have been described with respect to preferred embodiments, it is apparent that modifications and changes can be made thereto without departing from the spirit and scope of the invention as defined by the appended claims. For example, it is envisioned and well within the scope of the subject invention, that the system disclosed herein could be modified in such a manner so that the image tags associated with a web page could be substituted with modified image tags within the web server, rather than at the browser level.

What is claimed is:

1. A method for synchronizing the appearance of color images on a self-illuminating imaging device comprising the steps of:
   a) receiving a request for a color image from a web browser;
   b) forwarding the request for a color image to a web server;
   c) receiving a response to the request from the web server;
   d) modifying the response to facilitate color transformation of the color image based upon the color characteristics of the self-illuminating imaging device; and
   e) forwarding the modified response to the web browser for color transformation and display on the self-illuminating imaging device.

2. A method according to claim 1, wherein the step of modifying the response comprises the step of replacing the image tags associated with the color image with substitute image tags.

3. A method according to claim 2, further comprising the step of downloading a color management program to the web browser to perform color transformations utilizing the substitute image tags.

4. A method according to claim 1, further comprising the step of transforming the color image based upon the substitute image tags.

5. A method according to claim 1, further comprising the step of displaying the transformed color image on the self-illuminating imaging device.

6. A method according to claim 1, further comprising the step of generating a profile characterizing the color characteristics of the self-illuminating imaging device.

7. A method according to claim 6, further comprising the steps of:
   a) providing a set of color films each having a predetermined colorimetric reference value;
   b) sequentially placing each of the color films on the screen of the self illuminating imaging device within a region of predefined color bounded by a region of solid color;
   c) visually matching, in sequential order, each of the color films with the solid color boundary by adjusting the color settings of the self-illuminating imaging device; and
   d) generating an optimum color transformation for the self-illuminating imaging device based upon the color settings for each of the color films.

8. A method according to claim 7, further comprising the step of operatively associating the optimum color transformation with the web browser in the form of a profile represented by a set of numerical values describing the characteristics of the self-illuminating imaging device.

9. A method according to claim 8, further comprising the step of storing the profile as a cookie on a workstation associated with the self-illuminating imaging device.

10. A method according to claim 9, further comparing the step of storing the profile as an ICC profile in the memory of the workstation.

11. A method according to claim 6, further comprising the step of downloading a color characterization program to the web browser to facilitate generation of the profile.

12. A method according to claim 11, further comprising the step of embedding the color characterization program in an initial response forwarded to the web browser.

13. A method according to claim 6, further comprising the step of providing a color characterization program in the memory of a workstation operatively associated with the self-illuminating imaging device.

14. A method according to claim 1, further comprising the step of providing a color management program in the memory of a workstation operatively associated with the self-illuminating imaging device to perform color transformations utilizing the substitute image tags.

15. A method for color characterization of a self-illuminating imaging device comprising the steps of:
   a) receiving a request for a color image from a web browser;
   b) forwarding the request for a color image to a web server;
   c) receiving a response to the request from the web server; and d) embedding a color characterization program in the response to facilitate color characterization of a self-illuminating imaging device.

16. A method according to claim 15, further comprising the step of generating a profile characterizing the self-illuminating imaging device using the color characterization program.

17. A method according to claim 16, further comprising the steps of:
   a) providing a set of color films each having a predetermined colorimetric reference value;
   b) sequentially placing each of the color films on the screen of the self-illuminating imaging device within a region of predefined color bounded by a region of solid color;
   c) visually matching, in sequential order, each of the color films with the solid color boundary by adjusting the color settings of the self-illuminating imaging device; and
   d) generating an optimum color transformation for the self-illuminating imaging device based upon the color settings for each of the color films.

18. A method according to claim 17, further comprising the step of operatively associating the optimum color transformation with the web browser in the form of the profile represented by a set of numerical values describing the characteristics of the self-illuminating imaging device.

19. A method according to claim 18, further comprising the step of storing the profile as a cookie on a workstation associated with the self-illuminating imaging device.

20. A system for color characterization of a self-illuminating imaging device and synchronization of the appearance of color images on the self-illuminating imaging device comprising:
   a) a characterization stage including:
      i) means for embedding a color characterization program in a response to an initial browser based request for a color image to facilitate the color characterization of a self-illuminating imaging device associated with the browser;
      ii) means for forwarding the embedded response to a web browser;
      iii) means for generating a profile characterizing the self-illuminating imaging device using the color characterization program; and
      iv) means for storing the profile as a cookie on a workstation associated with the self-illuminating imaging device, wherein the cookie represents a set of twelve numerical profiling values; and
   b) a synchronization stage including:
      i) means for modifying a response to a subsequent browser based request for a color image by replacing the image tags associated with the color image with substitute image tags configured to effect a color transformation based upon the profile characterizing the self-illuminating imaging device;
      ii) means for forwarding the modified response to the web browser; and
      iii) means for transforming the color image based upon the substitute image tags for display on the self-illuminating imaging device.

21. A system as recited in claim 20, wherein the means for generating a profile characterizing the self-illuminating imaging device comprises a set of color films each having a predetermined calorimetric reference value for placement on the screen of the self-illuminating imaging device within a region of predefined color bounded by a region of solid color.

22. A system as recited in claim 21, further comprising a program for providing a region of predefined color bounded by a region of solid color on the screen of the self-illuminating imaging device, for each of a plurality of solid colors corresponding to the set of color films.

23. A system as recited in claim 21, wherein the each color film in the set include means for temporarily securing the film to the screen of the self-illuminating imaging device within the region of predefined color.

24. A method for color characterization of a self-illuminating imaging device and synchronizing the appearance of color images on a self-illuminating imaging device comprising the steps of:
   a) providing a color characterization program for communication with a web browser to facilitate color characterization of a self-illuminating imaging device operatively associated therewith; and
   b) providing a color management program for communication with the web browser to perform color transformations on color images received by the web browser based upon the color characterization of the self-illuminating imaging device.

25. A method according to claim 24, wherein the step of providing the color characterization program comprises downloading the color characterization program to the web browser from a web server.

26. A method according to claim 24, wherein the step of providing the color characterization program comprises storing the color characterization program on a workstation operatively to the web browser.

27. A method according to claim 24, wherein the step of providing the color management program comprises downloading the color management program to the web browser from a web server.

28. A method according to claim 24, wherein the step of providing the color management program comprises storing the color management program on a workstation operatively to the web browser.

29. A method according to claim 24, further comprising the step of modifying a response to a request for a color image from the web browser by replacing image tags associated with the color image with substitute image tags configured to facilitate color transformation of the color image based upon the color characteristics of the self-illuminating imaging device.

30. A method according to claim 24, further comprising the step of forwarding he modified response to the web browser for color transformation and display on the self-illuminating imaging device.

31. A method according to claim 24, further comprising the step of generating a profile characterizing the self-illuminating imaging device using the color characterization program.

32. A method according to claim 31, further comprising the steps of:
   a) providing a set of color films each having a predetermined colorimetric reference value;
   b) sequentially placing each of the color films on the screen of the self-illuminating imaging device within a region of nominal white color bounded by a region of solid color;
   c) visually matching, in sequential order, each of the color films with the solid color boundary by adjusting the color settings of the self-illuminating imaging device; and
   d) generating an optimum color transformation for the self-illuminating imaging device based upon the color settings for each of the color films.

33. A method according to claim 31, further comprising the step of operatively associating the optimum color transformation with the web browser in the form of the profile represented by a set of numerical values describing the characteristics of the self-illuminating imaging device.

34. A method according to claim 33, further comprising the step of storing the profile as a cookie on a workstation associated with the self-illuminating imaging device.

35. A method for color characterization of a self-illuminating imaging device comprising the steps of:
   a) receiving a request for a color image from a web browser;
   b) forwarding the request for a color image to a web server;
   c) receiving a response to the request from the web server; and
   d) embedding a color characterization program in the response to facilitate color characterization of a self-illuminating imaging device using a set of color films each having a predetermined calorimetric reference value.

36. A method according to claim 35, further comprising the step of generating a profile characterizing the self-illuminating imaging device using the color characterization program and the set of color films.

37. A method according to claim 36, further comprising the steps of:
   a) sequentially placing each of the color films on the screen of the self-illuminating imaging device within a region of nominal white color bounded by a region of solid color; and
   b) visually matching, in sequential order, each of the color films with the solid color boundary by adjusting the color settings of the self-illuminating imaging device, whereby the color profile for the self-illuminating imaging device is based upon the color settings for each of the color films.

38. A system for synchronizing the appearance of color images on a self-illuminating imaging device comprising:
   a) a workstation including a self-illumination imaging device;
   b) a web browser operatively associated with the workstation; and
   c) a color management program operatively associated with the web browser for performing color transformations, based upon the color characteristics of the self-illuminating imaging device, upon color images received by the web browser and displayed on the self-illuminating imaging device.

39. A system as recited in claim 38, wherein the color management program is downloaded to the web browser from a web server.

40. A system as recited in claim 38, wherein the color management program and the web browser are encoded on a computer-readable storage medium.

41. A system as recited in claim 38, wherein the color management program is resident in the memory of the workstation.

42. A method of characterizing an image display device comprising the steps of:
   a) providing a set of color reference means each having a predetermined reference value associated therewith;
   b) positioning each of the color reference means on a display surface;
   c) visually matching each of the color reference means with a color image displayed on the display surface by the image display device by selectively adjusting the color settings of the image display device; and
   d) generating a color profile for the image display device based upon the final color settings selected for each of the color reference means.

43. A method according to claim 42, wherein the step of providing a set of color reference means each having a predetermined reference value associated therewith comprises providing a set of color reference plates each having a predetermined spectral reflectance value associated therewith.

44. A method according to claim 42, wherein the step of providing a set of color reference means each having a predetermined reference value associated therewith comprises providing a set of transparent color reference films each having a predetermined colorimetric reference value associated therewith.

45. A method according to claim 43, wherein the step of positioning each of the color reference means on a display surface comprises positioning each color reference plate on a projection screen.

46. A method according to claim 44, wherein the step of positioning each of the color reference means on a display surface comprises positioning each of the transparent color reference films on a display screen of a self-illuminating imaging device.

47. A method according to claim 42, wherein the step of generating a color profile for the image display device comprises generating a color profile for an image projection device.

48. A method according to claim 42, wherein the step of generating a color profile for the image display device comprises generating a color profile for a self-illuminating imaging device.

49. A method according to claim 42, further comprising the step of storing the color profile for the image display device on a computer workstation operatively associated with the image display device.

* * * * *